(12) United States Patent
Timmons

(10) Patent No.: US 8,684,007 B2
(45) Date of Patent: Apr. 1, 2014

(54) ORAL APPLIANCE FOR THE TREATMENT OF SLEEP APNEA

(76) Inventor: William R. Timmons, Crofton, MD (US)

( * ) Notice: Subject to any disclaimer, the term of this patent is extended or adjusted under 35 U.S.C. 154(b) by 332 days.

(21) Appl. No.: 13/076,048

(22) Filed: Mar. 30, 2011

(65) Prior Publication Data

US 2012/0247485 A1 Oct. 4, 2012

(51) Int. Cl.
*A61F 5/56* (2006.01)
*A61C 5/14* (2006.01)

(52) U.S. Cl.
USPC ............ 128/848; 128/860; 128/861; 433/140

(58) Field of Classification Search
USPC ............ 128/848, 205.24, 859–863; 602/902; 433/6, 19, 140, 93
See application file for complete search history.

(56) References Cited

U.S. PATENT DOCUMENTS

| | | | | |
|---|---|---|---|---|
| 2,588,169 | A | * | 3/1952 | Shea .............................. 433/214 |
| 3,132,647 | A | * | 5/1964 | Corniello ...................... 128/848 |
| 3,768,477 | A | | 10/1973 | Anders et al. |
| 4,718,662 | A | | 1/1988 | North |
| 5,042,506 | A | | 8/1991 | Liberati |
| 5,316,020 | A | | 5/1994 | Truffer |
| 5,409,017 | A | | 4/1995 | Lowe |
| 5,692,523 | A | * | 12/1997 | Croll et al. ..................... 128/859 |
| 5,915,385 | A | | 6/1999 | Hakimi |
| 5,921,241 | A | | 7/1999 | Belfer |
| 6,092,523 | A | | 7/2000 | Belfer |
| 6,170,485 | B1 | | 1/2001 | Orrico |
| 6,997,186 | B2 | * | 2/2006 | Robertson et al. ....... 128/204.18 |
| 7,143,767 | B2 | | 12/2006 | Zacco |
| D554,260 | S | | 10/2007 | Diacopoulos et al. |
| 7,328,698 | B2 | | 2/2008 | Scarberry et al. |
| 7,448,388 | B2 | | 11/2008 | Halstrom |
| 2007/0292819 | A1 | * | 12/2007 | Scarberry et al. ............. 433/140 |
| 2008/0041396 | A1 | | 2/2008 | Lucker |
| 2008/0153056 | A1 | | 6/2008 | Baldwin |
| 2009/0098508 | A1 | | 4/2009 | Baldwin |
| 2009/0120446 | A1 | | 5/2009 | Vaska et al. |

FOREIGN PATENT DOCUMENTS

GB 1569129 6/1980

OTHER PUBLICATIONS

Website, http://www.dentalsleepapnea.com/Oral Appliance_Therapy.htm, series of seven different sleep apnea treatment devices, 5 of 13 pages printed from the internet on Jan. 17, 2010.

* cited by examiner

*Primary Examiner* — Patricia Bianco
*Assistant Examiner* — Kari Petrik
(74) *Attorney, Agent, or Firm* — Richard C. Litman

(57) ABSTRACT

The oral appliance for the treatment of sleep apnea provides greater comfort to the user and maintains an open air passage through the mouth by preventing the tongue from blocking the windpipe during sleep. The appliance has a mouthpiece including a frame of hard material and a tooth tray of softer material that conforms closely to the tooth pattern of the user. A spoon-like tongue depressor extends adjustably from the forward center of the device, the tongue depressor having a downward convex bowl that holds the tongue away from the windpipe of the user. The tongue depressor has a stein captured by and rotating in the adjuster, so that the tongue depressor may be prevented from rotating as the adjuster is threaded inwardly or outwardly in the front of the device. An air passage is preferably provided to each side of the tongue depressor adjuster.

4 Claims, 2 Drawing Sheets

ORAL APPLIANCE FOR THE TREATMENT OF SLEEP APNEA

BACKGROUND OF THE INVENTION

1. Field of the Invention

The present invention relates generally to devices for treatment of sleep disorders, and more particularly to an oral appliance for the treatment of sleep apnea.

2. Description of the Related Art

Many people consider sleep apnea to be essentially a condition of snoring or loud breathing during sleep, and thus to be nothing more than an annoyance to those sleeping (or trying to sleep) nearby. However, the term apnea refers to the (momentary) cessation of breathing, sleep apnea being such momentary cessation of breathing during sleep. Severe sleep apnea can deprive the sleeper of sufficient oxygen for a restful sleep, and the sudden cessation will usually cause the sleeper to awake. Several episodes a night will deprive the sleeper of sufficient sleep to function alertly the next day. Yet, such sleep apnea is generally a chronic condition, and it can be difficult to find a solution in many cases.

Sleep apnea may have various base causes. One such cause is the momentary blockage of the windpipe by the tongue, which may occur particularly when the sleeper is already breathing through his or her mouth. While this is almost never fatal, it nevertheless creates an apnea episode and interrupts sound sleep. As a result, a number of devices have been developed in the past to treat such episodes of sleep apnea, ranging from mechanical devices intended for placement in the mouth to restrain movement of the tongue to more complex and costly devices, such as continuous positive airway pressure machines and other electronic devices. Most of the simpler mechanical devices hold the lower jaw forward to draw the tongue forward as well, which is uncomfortable to say the least. Many potential users are unable to accustom themselves to the use of such appliances. The more costly and complex electronic devices are beyond the means of many people who could benefit from such devices. Yet, medical insurance may not cover such devices, as sleep apnea is generally not a life-threatening condition except in the most extreme cases.

Thus, an oral appliance for the treatment of sleep apnea solving the aforementioned problems is desired.

SUMMARY OF THE INVENTION

The oral appliance for the treatment of sleep apnea comprises a generally U-shaped mouthpiece having indentations therein for the upper and lower teeth, much like a mouth guard used in many sports. The mouthpiece is formed as two components, including an outer component or frame formed of a relatively hard plastic or other suitable material and an inner component or tooth tray formed of a softer plastic that is preferably molded or formed to closely fit the specific tooth pattern of the user. The two components are molded or otherwise formed as mutually integral parts with one another.

A tongue depressor extends rearwardly from an adjuster in the forward center portion of the mouthpiece. The tongue depressor has a generally spoon-shaped bowl having a convex lower surface resting upon the tongue to hold the tongue forwardly of the windpipe. The adjuster comprises a threaded sleeve having a correspondingly threaded cylinder therein, adjustable by a small tool, such as a small screwdriver or the like. The tongue depressor has a stem including a head that is captured and rotates in the cylinder of the adjuster, allowing the adjuster to be threaded inwardly and outwardly, the depressor being restrained from rotation. At least one air passage is provided through the front of the mouthpiece, preferably two air passages, one being located on each side of the adjuster.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
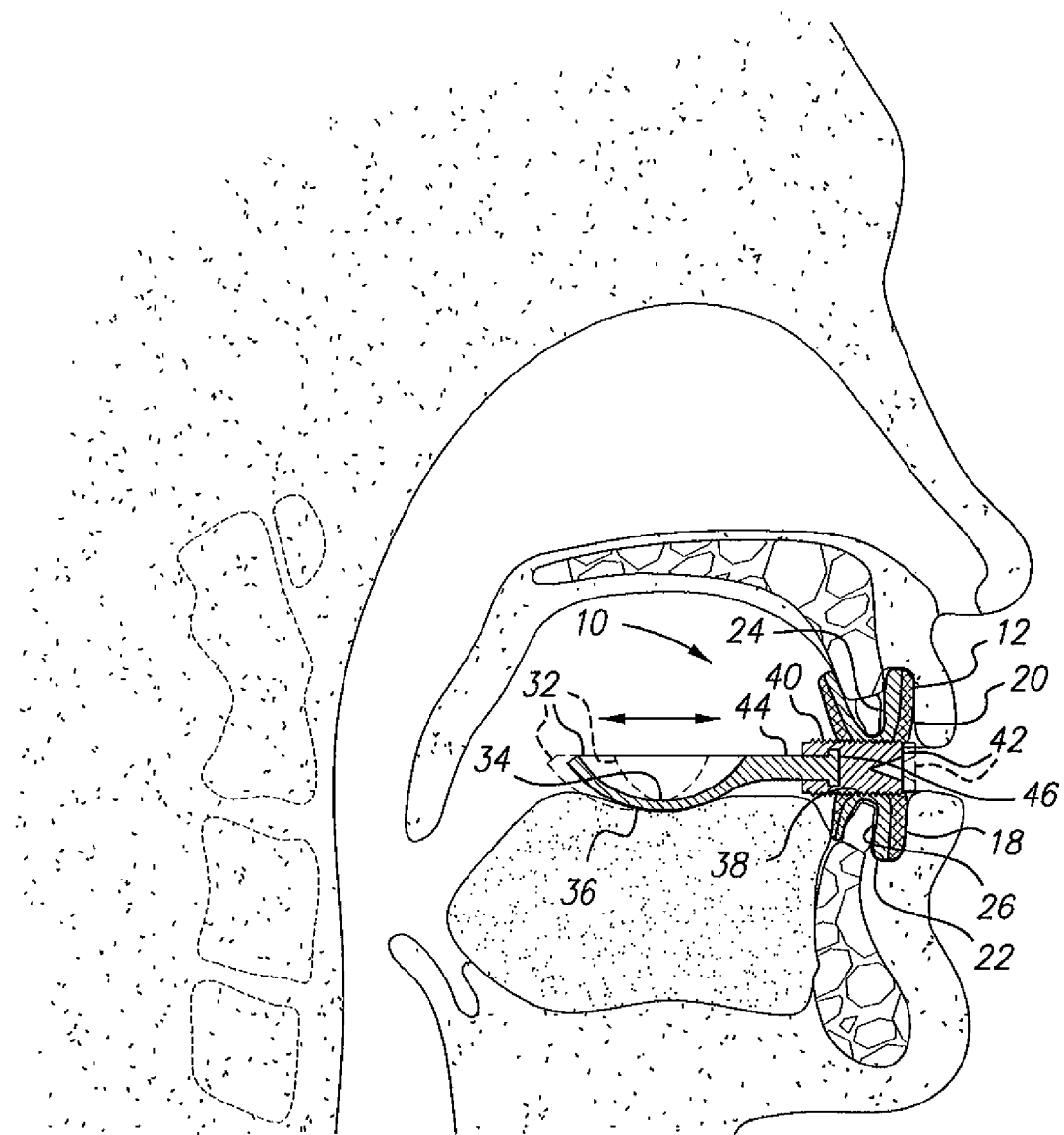
FIG. 1 is an environmental right side elevation view in section of the forward center portion of an oral appliance for the treatment of sleep apnea according to the present invention, showing the fit of the forward center portion and the tongue depressor in the mouth of an individual.
Figure 2:
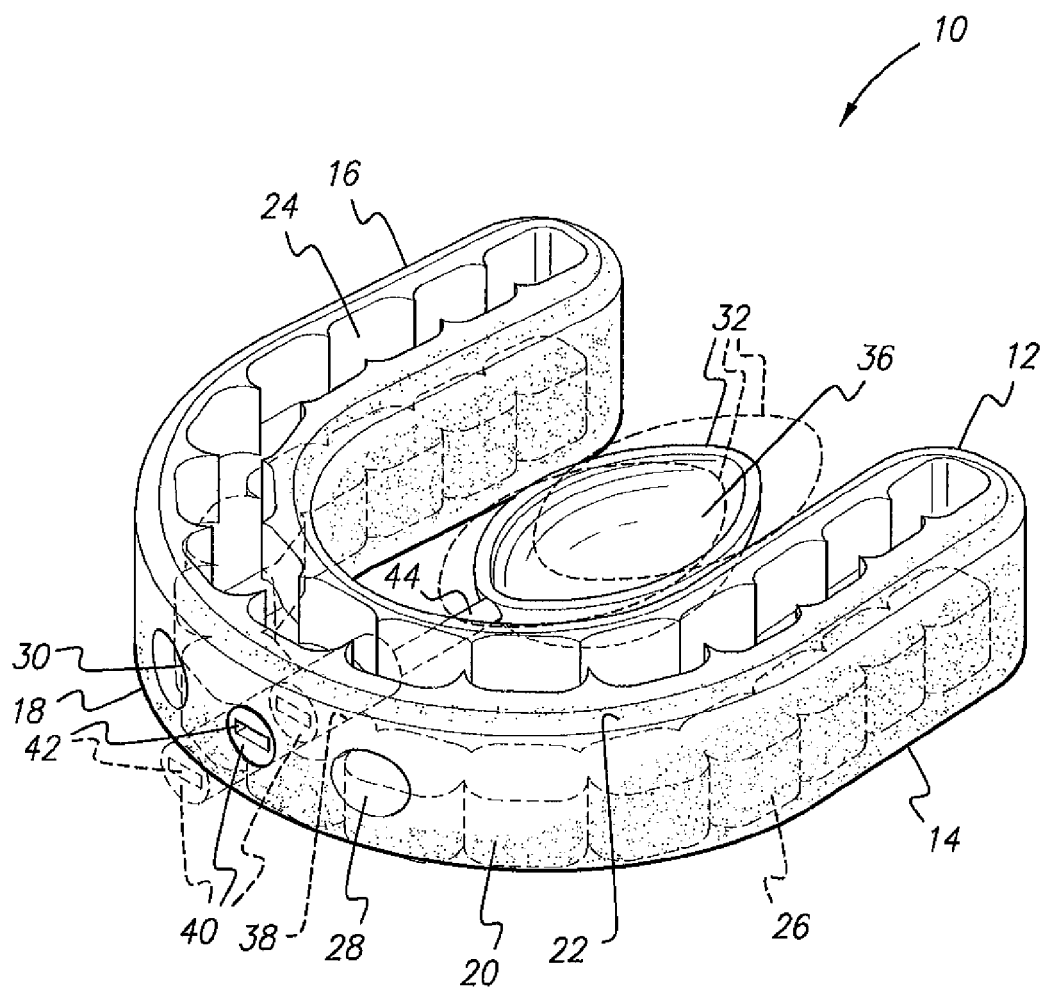
FIG. 2 is a perspective view of an oral appliance for the treatment of sleep apnea of FIG. 1, showing further details thereof.

The oral appliance for the treatment of sleep apnea is placed in the mouth of a person subject to sleep apnea, and assists in restricting rearward tongue movement to maintain a clear airway passage for the sleeper who may breathe through his or her mouth. FIG. 1 provides an environmental view in section of the forward center portion of the appliance and the tongue depressor extending rearwardly therefrom, shown in the mouth of an individual. FIG. 2 is a detailed perspective view of the appliance, showing further features and details.

The oral appliance 10 comprises a mouthpiece 12 having a left lateral portion 14, an opposite right lateral portion 16, and a forward center portion 18. The mouthpiece 12 is generally U-shaped and conforms at least generally to the upper and lower jaw of a person using the device. The mouthpiece 12 is actually formed of two components that are integrally bonded together. An outer frame 20 is preferably formed of a hard, plastic, biocompatible compound acceptable for use in the mouth. Alternatively, other materials (e.g., metal, etc.) may be used. The frame 20 serves as a seat or receptacle for a tooth tray 22 formed of a softer, more resilient material. The tooth tray 22 is preferably cast by a medical professional (e.g., dentist) to conform closely to the upper and lower teeth of the user of the device 10. The tooth tray 22 has an upper row 24 and an opposite lower row 26 of tooth indentations cast therein when it is formed. The resilient nature and precise fit of the tooth tray 22 provide maximum comfort for the person using the device.

The forward center portion 18 of the mouthpiece 12 preferably includes a pair of laterally offset breathing passages 28 and 30 disposed therethrough, to allow a sleeper using the device to breathe through his or her mouth, should that be necessary. Thus, even though the close fit of the appliance 10 precludes sufficient intake of air around the device when it is being worn, the air passages 28 and 30 allow the user of the device to freely inhale and exhale orally during sleep. It will be seen that as few as one such passage 28 or 30 may be provided, or more than two such passages, if desired.

An adjustable tongue depressor 32 extends rearwardly from the forward center portion 18 of the mouthpiece 12, and is disposed generally between the two lateral portions 14 and 16 of the mouthpiece and is coplanar therewith. The tongue depressor 32 has a generally spoon-like bowl, having a downwardly convex lower or tongue contact surface 34 and an upper concave surface 36 opposite the convex tongue contact surface 34. This maximizes the height of the air passage through the mouth, between the roof of the mouth and the tongue depressor 32.

The forward center portion 18 of the mouthpiece 12 includes means for adjusting the tongue depressor 32. A threaded passage 38 is formed through the forward center 18 of the mouthpiece 12, and a mating threaded adjuster 40 is installed in the passage 38. The adjuster 40 includes a tool receptacle 42 (e.g., a screwdriver slot, a hexagonal receptacle for an Allen wrench, etc.) in the forward end thereof for threadably adjusting the adjuster 40 in or out of its passage 38. A stem 44 extends from the tongue depressor 32 to the adjuster 40. The stein 44 has a larger diameter head 46 that is captured within the adjuster 40. The stem 44 and its head 46 are separate components from the adjuster 40, the adjuster 40 being free to rotate relative to the tongue depressor stem 44 and its head 46 during adjustment. The tongue depressor 32, its stein 44 and stem head 46, and the adjuster 40 are all preferably formed of corrosion-resistant steel or other suitable material to prevent corrosion and deterioration in the moist environment of the mouth.

The above-described mechanism allows the forward and rearward position of the tongue depressor 32 to be adjusted relative to the forward center portion 18 of the mouthpiece 12. Assuming conventional right-hand threads for the passage 38 and adjuster 40, clockwise rotation of the adjuster 40 results in the inward advance of the adjuster 40 into the forward center portion 18 of the mouthpiece 12, thus adjusting the tongue depressor 32 rearwardly in the mouthpiece 12. Conversely, counterclockwise adjustment of the adjuster 40 will draw the adjuster 40 forward in the passage 38, thus repositioning the tongue depressor farther forward in the mouthpiece 12. These adjustments may be made by a medical professional when fitting the appliance, based upon his or her experience with the patient, or may be accomplished by the user of the device to maximize comfort and effect.

It is to be understood that the present invention is not limited to the embodiment described above, but encompasses any and all embodiments within the scope of the following claims.

I claim:

1. An oral appliance for the treatment of sleep apnea in a user, comprising:

a generally U-shaped mouthpiece adapted for conforming generally to an upper and lower jaw of the user, the mouthpiece having a forward center portion and left and right lateral portions extending rearwardly from the center portion thereby defining legs of the U-shaped mouthpiece, the mouthpiece including a frame and a tooth tray formed integrally with the frame, wherein the frame is formed of the material having a predetermined hardness and the tooth tray is formed of a material having a hardness less than the predetermined hardness of the frame, the tooth tray having tooth indentations formed therein adapted to closely fit upper and lower teeth of the user; and a tongue depressor extending rearwardly from the forward center portion of the mouthpiece, the depressor being centered generally between the left and right lateral portions of the mouthpiece, generally coplanar therewith, wherein the forward center section of the mouthpiece has a threaded passage defined therein, the tongue depressor further comprising:

a threaded adjuster disposed within the passage defined in the center section of the mouthpiece; and a stem extending forward from the tongue depressor, the stem having a head captured within the adjuster;

wherein selective rotation of the adjuster threadably adjusts the adjuster selectively inward and outward relative to the passage and the mouthpiece, thereby selectively adjusting the stem and tongue depressor forward and rearward relative to the forward center section of the mouthpiece.

2. The oral appliance for the treatment of sleep apnea according to claim 1, wherein the tongue depressor comprises a bowl having a downwardly convex tongue contact surface and an upwardly concave surface opposite the tongue contact surface.

3. The oral appliance for the treatment of sleep apnea according to claim 1, wherein the mouthpiece has at least one breathing passage defined therein, the at least one breathing passage being laterally offset from the tongue depressor.

4. The oral appliance for the treatment of sleep apnea according to claim 1, wherein the adjuster, the tongue depressor, the stern, and the head of the stem are formed of corrosion-resistant steel.

* * * * *